United States Patent
Yoshida et al.

(10) Patent No.: US 8,511,143 B2
(45) Date of Patent: Aug. 20, 2013

(54) GAS SENSOR INCLUDING A SEALED PEDESTAL PORTION

(75) Inventors: Shingo Yoshida, Ichinomiya (JP); Hidekazu Minami, Kasugai (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 13/444,432

(22) Filed: Apr. 11, 2012

(65) Prior Publication Data

US 2012/0260720 A1 Oct. 18, 2012

(30) Foreign Application Priority Data

Apr. 12, 2011 (JP) ................................ 2011-088376

(51) Int. Cl.
*G01D 11/24* (2006.01)
(52) U.S. Cl.
USPC ...................................................... 73/31.05
(58) Field of Classification Search
USPC ............................................ 73/23.31, 31.05
See application file for complete search history.

(56) References Cited

U.S. PATENT DOCUMENTS

2011/0061443 A1 3/2011 Minami et al.

FOREIGN PATENT DOCUMENTS

JP 2011-64587 A 3/2011

*Primary Examiner* — Lisa Caputo
*Assistant Examiner* — Punam Roy
(74) *Attorney, Agent, or Firm* — Sughrue Mion, PLLC

(57) ABSTRACT

A circuit section of a $NO_x$ sensor has an output base including a pedestal portion which projects from a middle part of a support surface of a base portion. A circuit board on which a storage medium storing individual information of the $NO_x$ sensor is mounted is arranged on a mount surface of the pedestal portion. The circuit section has a seal portion which is arranged above the support surface of the base portion, and which covers the circuit board from upper and lateral sides, thereby watertightly sealing the circuit board. The seal portion has an enclose portion which, in a state where the enclose portion protrudes from a peripheral edge of the support surface to a second circumferential side surface of the base portion, encloses the base portion along the peripheral edge.

4 Claims, 9 Drawing Sheets

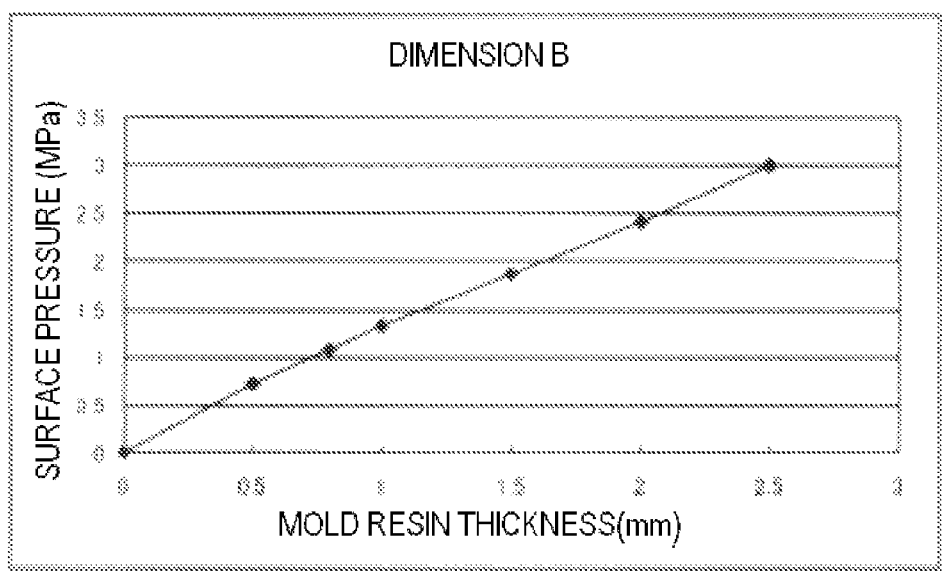

GAS SENSOR INCLUDING A SEALED PEDESTAL PORTION

BACKGROUND OF THE INVENTION

1. Field of the Invention

The present invention relates to a sensor which detects a specific component in a detection target gas.

2. Description of the Related Art

Conventionally, a gas sensor has been known which detects the concentration of a specific gas component in a detection target gas (for example, the concentration of $NO_x$ in an exhaust gas) from an internal combustion engine. In such a gas sensor, a sensing element which produces a signal corresponding to the concentration of the specific gas component, a heater which heats the sensing element, and the like are disposed. The concentration of the specific gas component is detected based on the signal which is output from the sensing element heated by the heater.

In such a gas sensor, variations between individual gas sensors may exist in the gas concentration characteristics indicating a relationship between a signal from a sensing element and the concentration of the specific gas component, and that between the resistance of a heater and the temperature of the heater.

As a sensor other than the above-described gas sensor, a soot sensor is known which detects the concentration of soot in a detection target gas. Also, in such a soot sensor, variations between individual soot sensors may exist in the characteristics indicating a relationship between a signal from a sensing element and the concentration of soot in the detection target gas.

In the $NO_x$ sensor disclosed in Patent Reference 1, to address such variations, a storage medium is provided which stores individual information indicating the gas concentration characteristics, heater temperature characteristics, and the like of the $NO_x$ sensor. A sensor control device which controls the $NO_x$ sensor is configured so that the individual information is retrieved from the storage medium, and variations among individual sensors are corrected by using the individual information, to thereby more correctly detect the $NO_x$ concentration.

[Patent Reference 1] JP-A-2011-064587

3. Problems to be Solved by the Invention

In the $NO_x$ sensor disclosed in Patent Reference 1, a circuit section 100 having the storage medium which stores the individual information of the $NO_x$ sensor is placed in a connector to which a cable from the sensor control device is connected (see FIG. 7). In the circuit section 100, a circuit board 110 on which the storage medium 111 is mounted is placed on a mount surface 121 which is located in a top portion of an output base 120, and a first circumferential side surface 122 and a second circumferential side surface 123 which extends outwards beyond the first circumferential side surface 122 are formed on the side surface of the output base 120. The entire mount surface 121 and the first circumferential side surface 122 are covered by a seal portion 130 made of a thermoplastic resin, thereby maintaining the circuit section 100 watertight.

In the $NO_x$ sensor disclosed in Patent Reference 1, however, the seal portion 130 in the circuit section 100 is placed so that the outer surface 131 of the sear portion 130 extends along the second circumferential side surface 123, and the abutment surface between the seal portion 130 and the output base 120 does not reach the second circumferential side surface 123. When the seal portion 130 contracts due to a temperature change in the circumference of the circuit section 100, therefore, there is a possibility of the seal portion 130 peeling off from the vicinity of the boundary between the first and second circumferential side surfaces 122, 123.

SUMMARY OF THE INVENTION

The present invention has been made in view of the above-discussed problems. It is an object of the invention to provide a sensor having a sealing structure which can suppress such peeling.

The above objection of the invention has been achieved by providing a sensor which includes: a sensing element which detects a specific component in a detection target gas; a circuit board on which a storage medium is mounted, the storage medium storing individual information related to the sensing element; an output base having: a pedestal portion on which the circuit board is placed; and a base portion in which a support surface is formed, the pedestal portion projecting from a middle part of the support surface; and a seal portion which is arranged above the support surface in a state where the seal portion covers the pedestal portion from upper and lateral sides, and which maintains the circuit board watertight. The seal portion has an enclose portion which, in a state where the enclose portion protrudes from a peripheral edge of the support surface of the base portion, to a side surface of the base portion intersecting with the support surface at the peripheral edge, encloses the side surface along the peripheral edge.

According to the above configuration, when contraction of the seal portion occurs due to an ambient temperature change, the enclose portion which encloses the base portion of the output base contracts to further compress the circumference of the base portion. Therefore, the enclose portion is hardly susceptible to peeling off from the side surface, whereby the seal portion can be suppressed from peeling off from the output base. Moreover, the increased compression of the enclose portion against the circumference of the base portion enhances a close contact force between the enclose portion and the side surface of the base portion, and the waterproof effect of the seal portion can be strengthened.

However, there is a concern that, when the compression of the enclose portion against the base portion is increased by contraction of the seal portion, a stress is produced in the abutment surface of the enclose portion with respect to the base portion. Particularly in the case where the boundary between the support surface of the base portion and the side surface of the base portion which is covered by the enclose portion is formed as an edge (an edge having an angle of 90°), when contraction occurs in the seal portion, the stress is concentrated in the abutment portion of the seal portion against the edge, and there is a possibility that a crack may occur in the seal portion.

Therefore, in a preferred embodiment, the sensor of the invention is characterized in that a chamfered portion is formed in the peripheral edge of the support surface of the base portion.

According to this configuration, when contraction of the seal portion occurs due to an ambient temperature change, it is possible to prevent a large stress from being produced in the abutment portion against the peripheral edge of the support surface in the seal portion, and formation of a crack or the like in the seal portion can be prevented. The chamfered portion may be formed as an R-chamfered portion, or as a C-chamfered portion.

For example, the seal portion may be formed by filling the circumference of the pedestal portion and the space above the base portion with a thermoplastic resin. When a chamfered portion is formed in the peripheral edge of the support surface, the thermoplastic resin is allowed to easily reach the circumference of the pedestal portion and the space above the base portion.

In another preferred embodiment of the sensor of the invention, the enclose portion has a length of at least 0.1 mm in the projection direction of the pedestal portion.

In yet another preferred embodiment of the sensor of the invention, the enclose portion has a thickness of at least 0.1 mm.

According to this configuration, it is possible to effectively enhance surface pressure by the enclose portion against the side surface of the base portion in the case where contraction of the seal portion occurs due to an ambient temperature change. Therefore, the seal portion can be suppressed more surely from peeling off from the output base, and the waterproof effect of the seal portion can be strengthened.

BRIEF DESCRIPTION OF THE DRAWINGS

FIGS. 4B and 4C are graphs showing results of simulations of a surface pressure produced in the seal portion in the case where the dimensions are changed.

DESCRIPTION OF REFERENCE NUMERALS AND SIGNS

Figure 1:
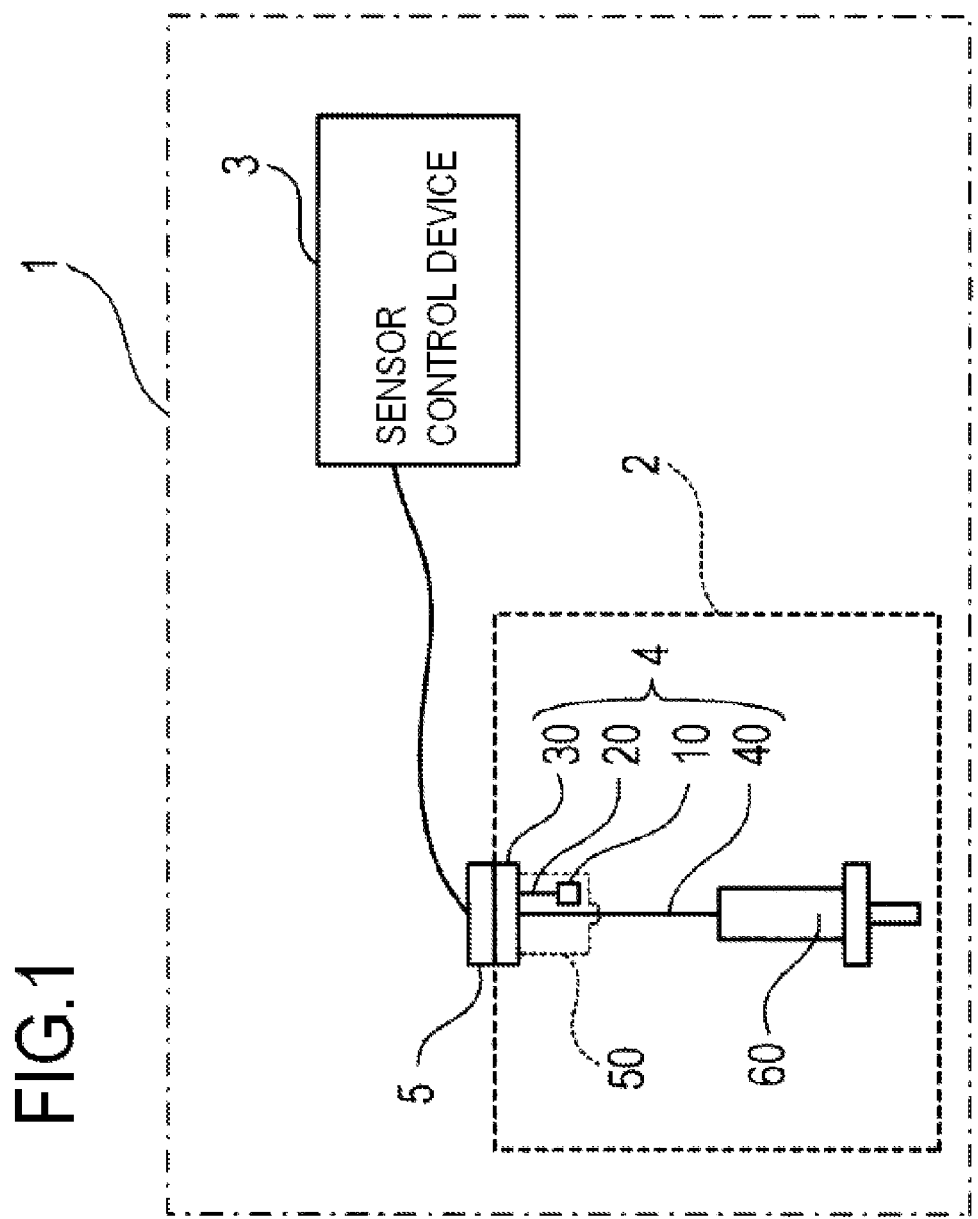
FIG. 1 is a diagram schematically showing the configuration of a gas sensing apparatus including a $NO_x$ sensor.

Reference numerals used to indicate various structural features in the drawings include:
1 . . . gas sensing apparatus, 2 . . . $NO_x$ sensor, 3 . . . sensor control device, 4 . . . connection cable section, 5 . . . connector, 10 . . . circuit section, 11 . . . output base, 12 . . . pedestal portion, 12a . . . mount surface, 12b . . . first circumferential side surface, 12c . . . projecting portion, 13 . . . base portion, 13a . . . second circumferential side surface, 13b . . . support surface, 13c . . . chamfered portion, 14 . . . case portion, 15 . . . seal portion, 15a . . . enclose portion, 16 . . . circuit board, 16a . . . through hole, 17 . . . storage medium, 20 . . . second lead line, 21 . . . terminal portion, 30 . . . connector, 31 . . . insertion face, 32 . . . fitting face, 40 . . . first lead line, 50 . . . connector boot, 51 . . . opening portion, 52 . . . accommodating portion, 53 . . . takeout portion, 60 . . . sensing element, 70 . . . bracket.

DETAILED DESCRIPTION OF THE INVENTION

Hereinafter, an embodiment of the invention will be described with reference to the drawings. However, the present invention should not be construed as being limited thereto.

Whole Configuration

FIG. 1 is a diagram schematically showing the configuration of a gas sensing apparatus 1 including a $NO_x$ sensor 2 to which the invention is applied.

As shown in FIG. 1, the gas sensing apparatus 1 includes the $NO_x$ sensor 2 which is disposed in an exhaust path of a burning application such as an internal combustion for a vehicle, or a boiler, and which detects the concentration of nitrogen oxide ($NO_x$) as the concentration of a specific gas component in exhaust gas, and a sensor control device 3 which controls the $NO_x$ sensor 2.

The $NO_x$ sensor 2 includes: a sensing element 60 which outputs a concentration signal corresponding to the $NO_x$ concentration to the sensor control device 3; a connection cable section 4 having a connector 30 which is connected to the sensing element 60 through first lead lines 40; and a connector boot 50 which is attached to the connection cable section 4.

The connector 30 has a configuration in which the connector is connectable to and disconnectable from a connector 5 that is disposed in one end of a lead line connected to the sensor control device 3. When the connector 30 is fittingly attached to the connector 5, the $NO_x$ sensor 2 and the sensor control device 3 are electrically connected to each other.

The connection cable section 4 has a circuit section 10 which is connected to the connector 30 through second lead lines 20, and which supplies and receives data to and from the sensor control device 3. The circuit section 10 stores individual information which is preset in order to correct variations between individual $NO_x$ sensors 2 (sensing elements 60), and is configured so as to supply the individual information to the sensor control device 3 in response to a request signal delivered from the sensor control device 3. Although there are a plurality of lead lines through which the connector 5 is connected to the sensor control device 3, such as the first lead lines 40 and the second lead lines 20, the lead lines are shown by a single line in FIG. 1 in order to facilitate understanding of the configuration of the gas sensing apparatus 1.

The sensing element 60 has a known configuration including: a sensor main unit having a first oxygen pumping cell, an oxygen partial pressure sensing cell, a second oxygen pumping cell, a first measuring chamber, a second measuring chamber, an oxygen reference chamber, and the like; and a heater which heats the sensor main unit. Each of the first oxygen pumping cell, the oxygen partial pressure sensing cell, and the second oxygen pumping cell has a configuration in which a pair of electrodes are disposed on a solid electrolyte layer that is oxygen ion conductive.

On the other hand, the sensor control device 3 includes: a sensor drive section which drives the first oxygen pumping cell, the oxygen partial pressure sensing cell, and the second oxygen pumping cell; a heater drive section which drives the heater; and a controlling section which controls the sensor drive section and the heater drive section.

The controlling section of the sensor control device 3 controls the temperature of the heater through the heater drive section, and controls the sensor drive section. A first pump current Ip1 flowing through the first oxygen pumping cell is obtained as a concentration signal indicating the oxygen concentration in a detection target gas, and a second pump current Ip2 flowing through the second oxygen pumping cell is obtained as a concentration signal indicating the $NO_x$ concentration in the detection target gas. Specifically, the sensor control device 3 controls the sensor drive section to control the first pump current Ip1 flowing to the first oxygen pumping cell so that an electromotive force produced in the oxygen partial pressure sensing cell in accordance with the oxygen concentration of an exhaust gas introduced into the first measuring chamber has a predetermined voltage (for example, 425 mV). Further, the sensor control device 3 adjusts the oxygen concentration in the first measuring chamber by means of an oxygen pumping operation performed by the first oxygen pumping cell. At this time, the sensor drive section detects the first pump current Ip1. The gas (adjustment gas) in which the oxygen concentration has been adjusted in the first measuring chamber flows into the second measuring chamber. A constant voltage (for example, 450 mV) is applied to the second oxygen pumping cell in which one electrode is placed in the second measuring chamber, and another electrode is placed outside the second measuring chamber, whereby $NO_x$ contained in the adjustment gas is dissociated. When oxygen produced in the dissociation of $NO_x$ by the second oxygen pumping cell is pumped out to the outside of the second measuring chamber, the sensor drive section detects the second pump current Ip2 flowing between the pair of electrodes.

The controlling section of the sensor control device 3 performs a concentration detecting process in which the oxygen concentration in the exhaust gas is detected based on the first pump current Ip1, and the $NO_x$ concentration is detected based on the second pump current Ip2. At this time, the concentration signal is corrected in accordance with the individual information of the sensing element 60 obtained from the circuit section 10 of the $NO_x$ sensor 2. Information ($O_2$ gain and $O_2$ offset) for setting characteristics representing relationships between the first pump current Ip1 and the oxygen concentration, ($NO_x$ gain and $NO_x$ offset) for setting characteristics representing relationships between the second pump current Ip2 and the NOx concentration, and the like may be used as the individual information. The controlling section sends the detected oxygen and $NO_x$ concentrations to an external apparatus (not shown, for example, an engine control unit).

Configuration of Circuit Section

Figure 2:
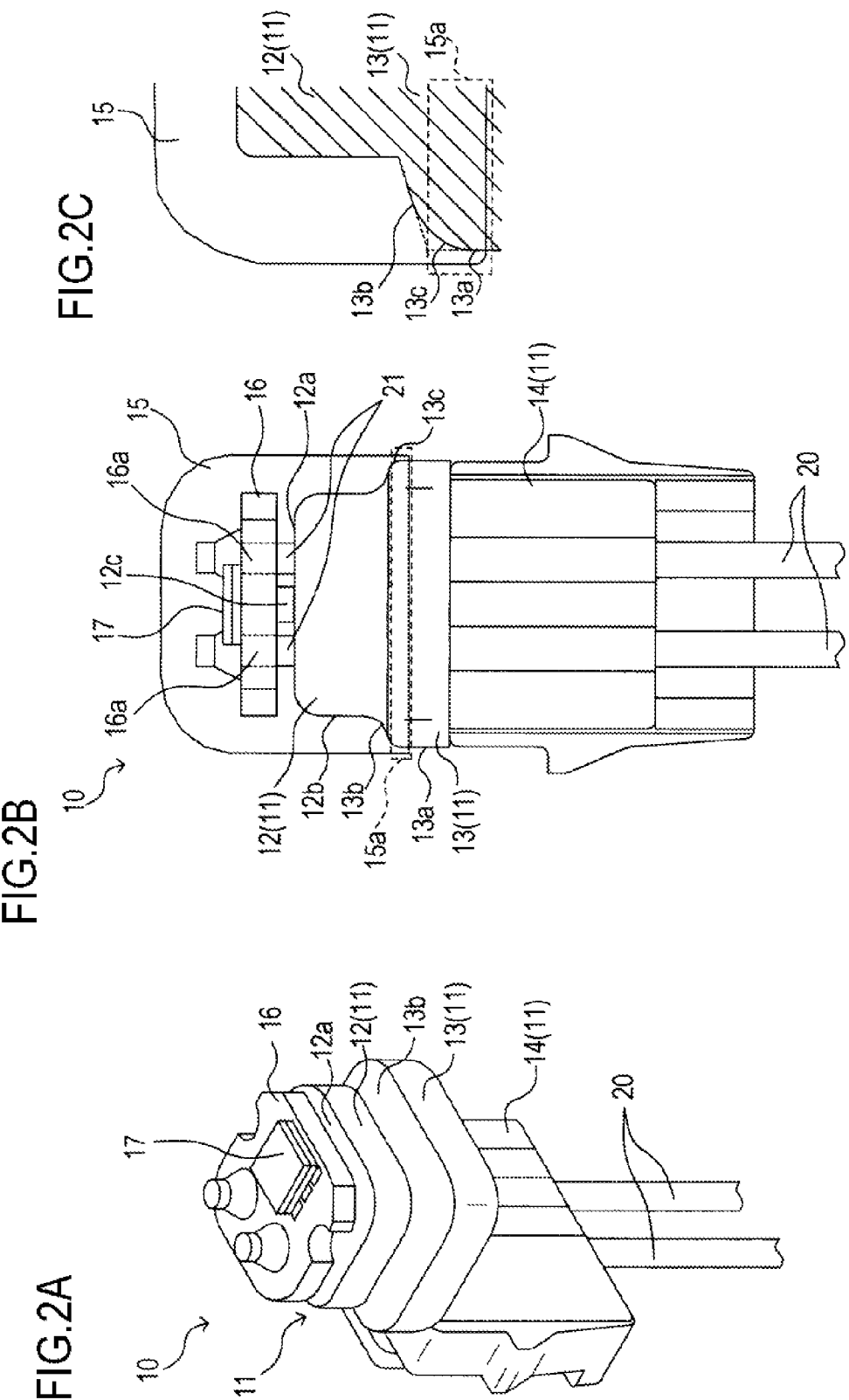
FIG. 2A is a perspective view showing the configuration of a circuit section in the $NO_x$ sensor.
FIG. 2B is a side elevation view of the circuit section.
FIG. 2C is a partial sectional view of the circuit section.

Next, the circuit section 10 will be described. FIG. 2A is a perspective view of the circuit section 10 in a state where a seal portion 15 which will be described later is not formed, and FIG. 2B is a side elevation view of the circuit section 10.

The circuit section 10 of the gas sensing apparatus 1 of the embodiment is different from the circuit section of the gas sensing apparatus disclosed in "DETAILED DESCRIPTION OF THE INVENTION" of Patent Reference 1, in the configurations of the seal portion 15 and the output base 11, and the other portions are similarly configured. Therefore, hereinafter, description will be made with placing emphasis on the different points.

As shown in FIGS. 2A and 2B, the circuit section 10 includes: a storage medium 17 which stores individual information related to the $NO_x$ sensor 2; a planar circuit board 16 on which the storage medium 17 is mounted; the output base 11 having a mount surface 12a on which columnar terminal portions 21 are penetratedly formed, the terminal portions 21 being connected to the second lead lines 20 and used for outputting the individual information from the storage medium 17; and the seal portion 15 which watertightly covers the circuit board 16.

The output base 11 is formed by using a nylon resin (for example, PA66 nylon) as a material, and includes: a case portion 14 for accommodating the second lead lines 20; a base portion 13 which is continuous to the case portion 14; and a pedestal portion 12 which projects from a middle part of a support surface 13b that is formed at a position of the base portion 13 opposed to the case portion 14. A cavity region (not shown) communicating with the inside of the case portion 14 is formed inside the base portion 13 and the pedestal portion 12. In the cavity region, the terminal portions 21 are connected to the second lead lines 20.

A top portion of the pedestal portion 12 is formed as the above-described mount surface 12a, and the pedestal portion 12 has a first circumferential side surface 12b which is continuous to the mount surface 12a and the support surface 13b of the base portion 13. The base portion 13 has a second circumferential side surface 13a which is continuous to the support surface 13b. The second circumferential side surface 13a is disposed so as to extend outward beyond the first circumferential side surface 12b, and the support surface 13b of the base portion 13 constitutes a step between the first and second circumferential side surfaces 12b, 13a. A chamfered portion (R-chamfered portion) 13c having a rounded shape is formed in the boundary (in other words, the peripheral edge of the support surface 13b) between the first and second circumferential side surfaces 12b, 13a.

The circuit board 16 has through holes 16a which extend through the circuit board 16 in the thickness direction. The terminal portions 21 are inserted into the through holes 16a, and then the surface opposed to that on which the storage medium 17 is mounted abuts against a projecting portion 12c projecting on the mount surface 12a of the pedestal portion 12, to be supported thereby. On the surface of the circuit board 16 on which the storage medium 17 is mounted, connection portions which are electrically connected to the storage medium 17 are disposed in the peripheral edges of the through holes 16a, and joined (for example, soldered) to the terminal portions 21.

In this way, the circuit board 16 is supported by the projecting portion 12c, so that a gap the size of which corresponds to the height of the projecting portion 12c is formed between the mount surface 12a of the output base 11 and the circuit board 16.

On the other hand, the seal portion 15 is formed by filling the space around the circuit board 16, the first circumferential side surface 12b, and the support surface 13b with a thermoplastic resin. The seal portion 15 is placed so as to, in a state where it is placed above the support surface 13b, cover the first circumferential side surface 12b of the pedestal portion 12 from the lateral side, and cover the circumference of the circuit board 16.

FIG. 2C is a diagram schematically showing sections of the seal portion 15, the base portion 13, and the pedestal portion 12. As shown in the diagram, the seal portion 15 protrudes from the peripheral edge (in the embodiment, the chamfered portion 13c) of the support surface 13b to extend over the second circumferential side surface 13a, to have an enclose portion 15a which, while contacting with the second circumferential side surface 13a, encloses the second circumferential side surface 13a along the peripheral edge (in other words, the chamfered portion 13c which is formed over the whole circumference of the boundary between the support surface 13b of the base portion 13 and the second circumferential side surface 13a).

Preferably, the enclose portion 15a has a thickness of 0.1 mm or more (more preferably, 0.5 mm or more), and the length (in the case where chamfering is not performed, the length from the peripheral edge of the support surface 13b to the end of the enclose portion 15a) of the enclose portion 15a in the projection direction of the pedestal portion 12 is 0.1 mm or more. Preferably, the thickness of the enclose portion 15a is set to be smaller than the length of the step between the first circumferential side surface 12b and the second circumferential side surface 13a, whereby the enclose portion 15a can be prevented from being laterally protruded in an excessive manner.

The thermoplastic resin forming the seal portion 15 is not particularly limited. In the embodiment, a hot-melt resin (for example, MACROMELT (registered trademark) of Henkel Japan Ltd.) having a thermal expansion coefficient which is higher than that of the nylon resin forming the output base 11 (the pedestal portion 12) is used.

Configuration of Connection Cable

Figure 3:
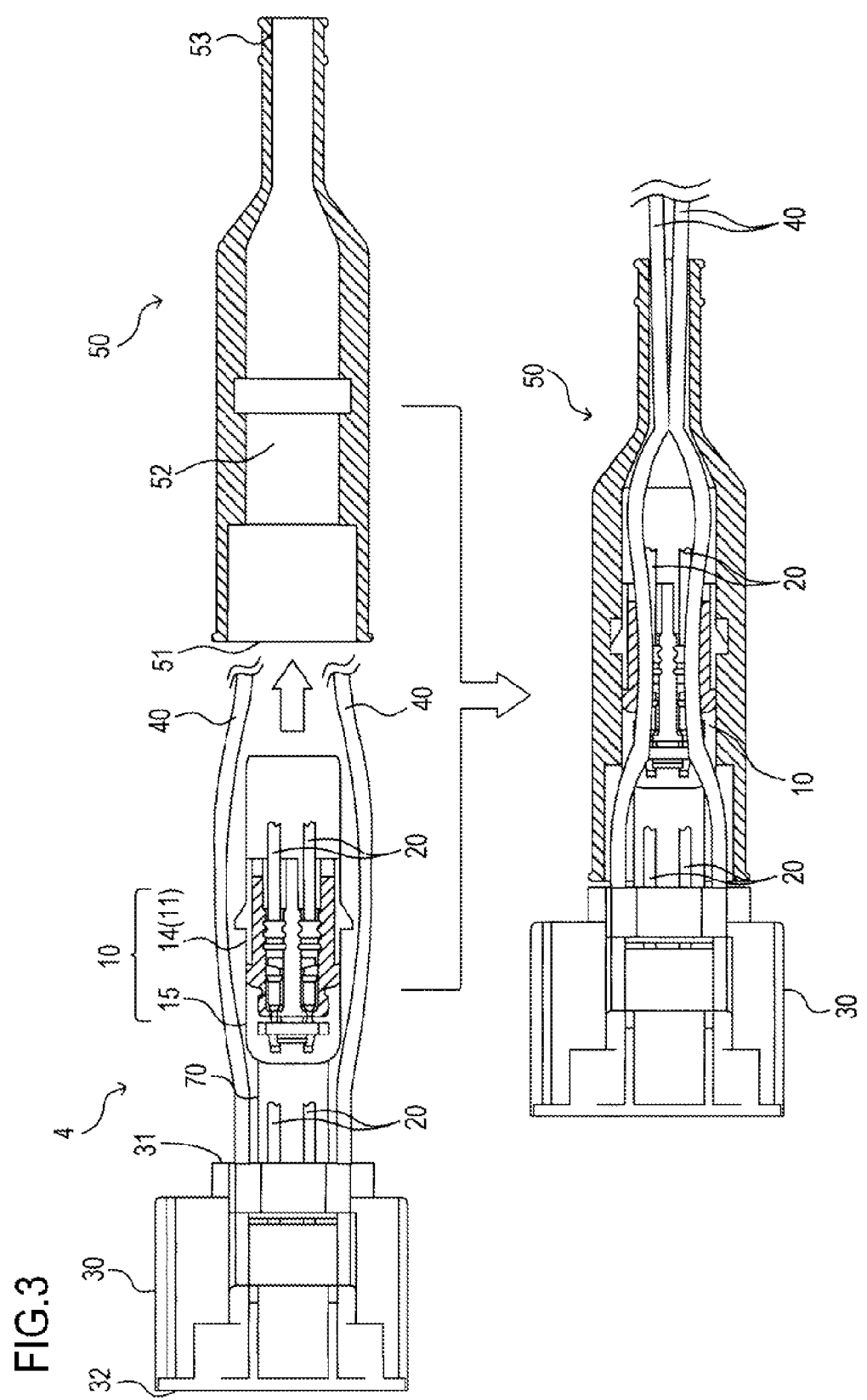
FIG. 3 is a sectional view showing the configurations of a connection cable section and the like in the $NO_x$ sensor.

Next, the connection cable section 4 which is placed in the connector boot 50 will be described. FIG. 3 is a view which shows a method of attaching the connector boot 50 to the connection cable section 4, in which the connection cable section 4 is seen from the upper side of the connector 30, and which shows in section the connector boot 50 and the circuit section 10 in the connection cable section 4.

In FIG. 3, only two first lead lines 40 are shown. In practice, a required number (in the embodiment, six) of first lead lines 40 corresponding to the configuration of the sensing element 60 are connected to the connector 30.

As shown in FIG. 3, in addition to the connector 30 and circuit section 10 which are described above, the connection cable section 4 includes a long plate-shaped (metal-made) bracket 70 for connecting the output base 11 constituting the circuit section 10 with the connector 30.

In the connector 30, formed are a fitting face 32 to which the connector 5 connected to the sensor control device 3 is fitted, an insertion face 31 where insertion holes into which the first and second lead lines 40, 20 are inserted, and a bracket attachment face for attaching the bracket 70.

The second lead lines 20 which are drawn out from the case portion 14 are bent in a direction opposite the direction along which the lead lines elongate in the case portion 14, and then inserted into the insertion holes of the insertion face 31, whereby the second lead lines 20 are electrically connected to the connector 30.

In the output base 11, by contrast, a bracket attachment surface which is used for attaching the bracket 70, and which is approximately rectangular is formed below the case portion 14. The output base 11 includes a holding portion for holding the bracket 70 on the bracket attachment surface.

The connection cable section 4 is inserted into the connector boot 50 for protecting the vicinities of places where the first and second lead lines 40, 20 are connected to the connector 30.

The connector boot 50 is a tubular elastic member made of rubber, and includes an opening portion 51 which encloses end portions of the first and second lead lines 40, 20 on the side where the lead lines are connected to the connector 30, and an accommodating portion 52 which accommodates the circuit section 10 and the second lead lines 20. The accommodating portion 52 also accommodates a part of the first lead lines 40 connected to the connector 30.

The connector boot 50 further includes a takeout portion 53 which is an opening portion for drawing out the first lead lines 40 from the accommodating portion 52. The first lead lines 40 drawn out from the takeout portion 53 are covered with a covering member (not shown) fitted on the takeout portion 53.

In the connector boot 50, the circuit section 10 and the first and second lead lines 40, 20 are accommodated in the accommodating portion 52, whereby dust and dirt are prevented from adhering to them, and adherence of water droplets thereto is reduced. The opening portion 51 encloses the first and second lead lines 40, 20, whereby the lead lines are prevented from being bent in the vicinity of the insertion face 31 of the connector 30.

Experimental Examples

According to the seal portion 15 of the circuit section 10 in the embodiment, when contraction of the seal portion 15 occurs, the second circumferential side surface 13a is compressed by the enclose portion 15a, and therefore the seal portion 15 is suppressed from peeling off from the output base 11. When it is configured so that, in contraction of the seal portion 15, the surface pressure against the abutment surface between the enclose portion 15a and the output base 11 is increased, the compression on the second circumferential side surface 13a by the enclose portion 15a can be further enhanced, and peeling off of the seal portion 15 can more surely be prevented from occurring.

By means of simulation, therefore, the surface pressure according to the dimensions of the seal portion 15 and the output base 11 in the case where the seal portion 15 is caused to contract by a temperature gradient (temperature change) from 110° C. to −10° C. was measured. A model of the circuit section 10 having the output base 11 in which the base portion 13 and the pedestal portion 12 are formed into a cylindrical shape was used in the simulation.

Figure 4A:
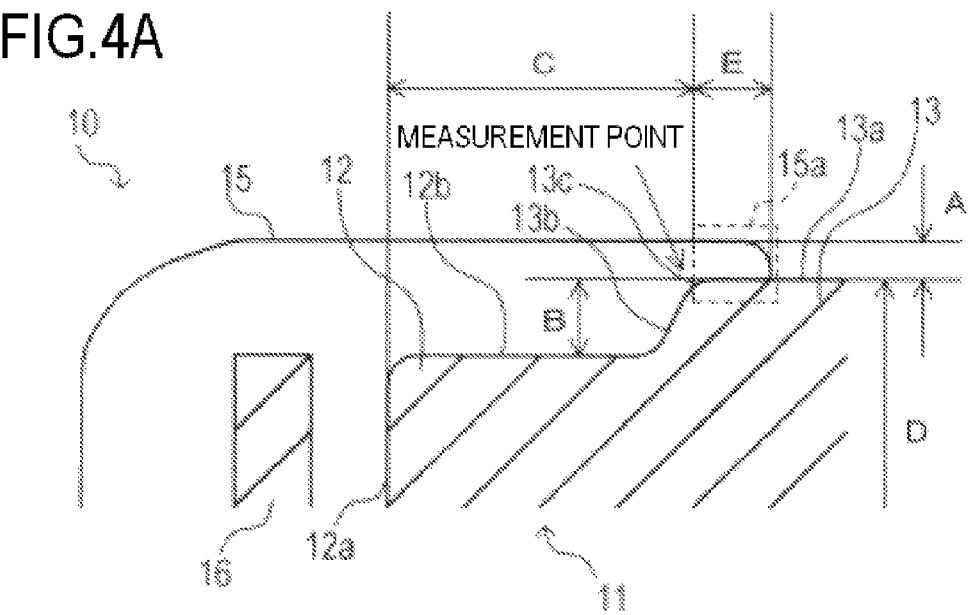
FIG. 4A is a diagram illustrating the dimensions of an output base and seal portion of the circuit section.

FIG. 4A is a diagram schematically showing a part of the output base 11 and the like.

As shown in the diagram, the thickness of the enclose portion 15a is indicated by A (unit: mm), the dimension of the step between the first and second circumferential side surfaces 12b, 13a is indicated by B (unit: mm), the length from the mount surface 12a of the pedestal portion 12 to the support surface 13b of the base portion 13 is indicated by C (unit: mm), the width of the base portion 13 is indicated by D (unit: mm), and the length of the enclose portion 15a in the projection direction of the pedestal portion 12 (the length from the peripheral edge of the support surface 13b to the end of the enclose portion 15a) is indicated by E (unit: mm). The peripheral edge of the support surface 13b of the base portion 13 was set as a measurement point. The surface pressure at the measurement point in the case where the sizes of A to E were changed was measured by means of simulation.

Although the chamfered portion 13c having a size of R=0.2 is formed in the peripheral edge of the support surface 13b of the base portion 13, C and E indicate the lengths from the peripheral edge in the case where the chamfered portion is not formed.

The graphs of FIGS. 4B, 4C, and 5A to 5C show results of the simulation.

Figure 4B:
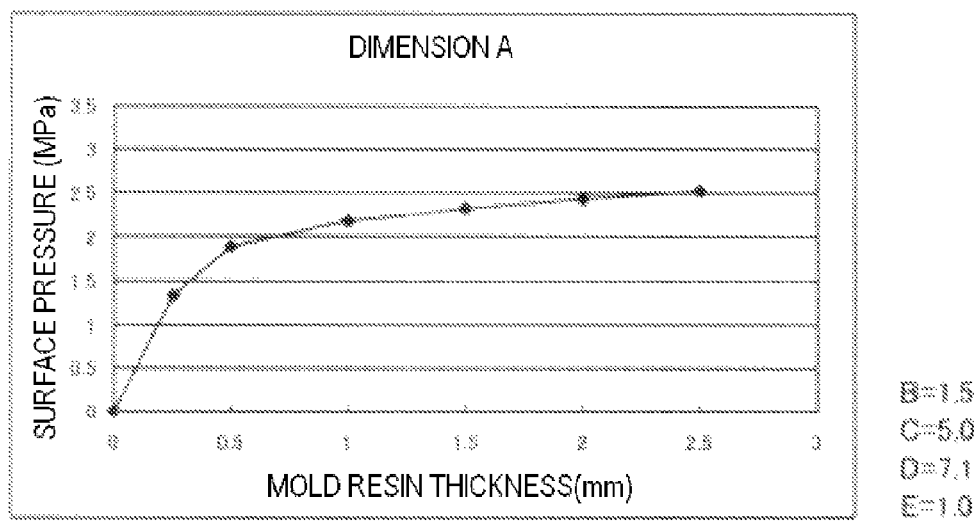

FIG. 4B shows the change of the surface pressure at the measurement point in the case where A is changed in the range from 0 to 2.5 mm in the state of B=1.5 mm, C=5.0 mm, D=7.1 mm, and E=1.0 mm.

FIG. 4C shows the change of the surface pressure at the measurement point in the case where B is changed in the range from 0 to 2.5 mm in the state of A=0.5 mm, C=5.0 mm, D=7.1 mm, and E=1.0 mm.

Figure 5A:
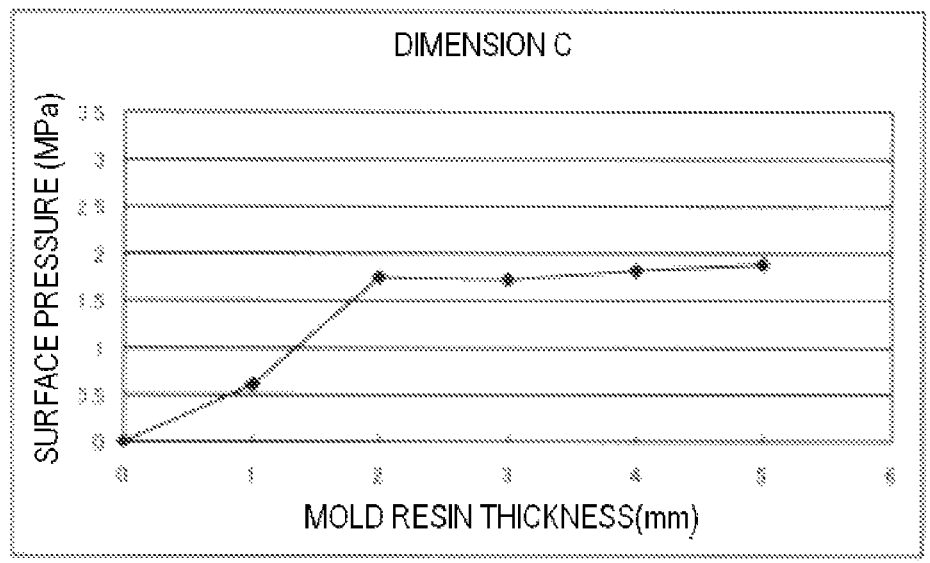
FIGS. 5A to 5C are graphs showing results of simulations of the surface pressure produced in the seal portion in the case where the dimensions of the output base and seal portion are changed.

FIG. 5A shows the change of the surface pressure at the measurement point in the case where C is changed in the range from 0 to 5 mm in the state of A=0.5 mm, B=1.5 mm, D=7.1 mm, and E=1.0 mm.

Figure 5B:
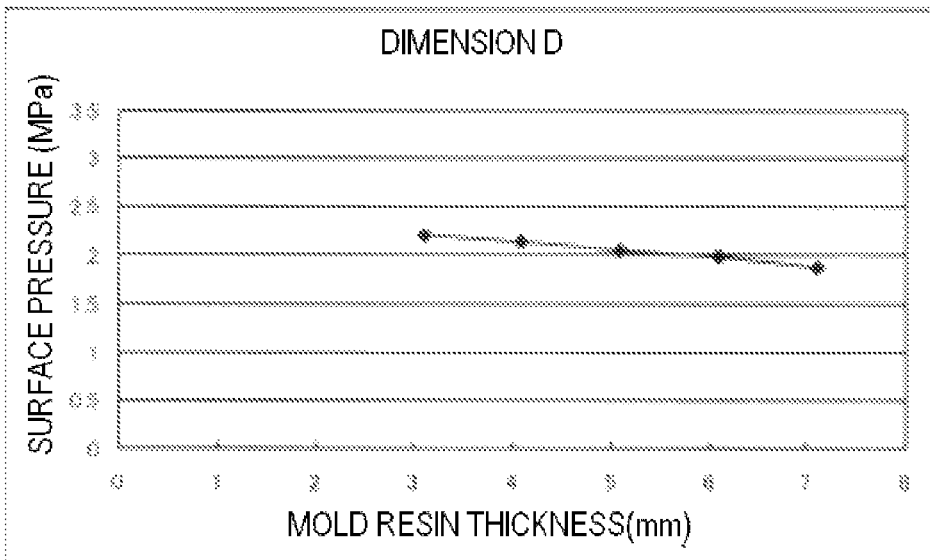

FIG. 5B shows the change of the surface pressure at the measurement point in the case where D is changed in the range from 3 to 7 mm in the state of A=0.5 mm, B=1.5 mm, C=5.0 mm, and E=1.0 mm.

Figure 5C:
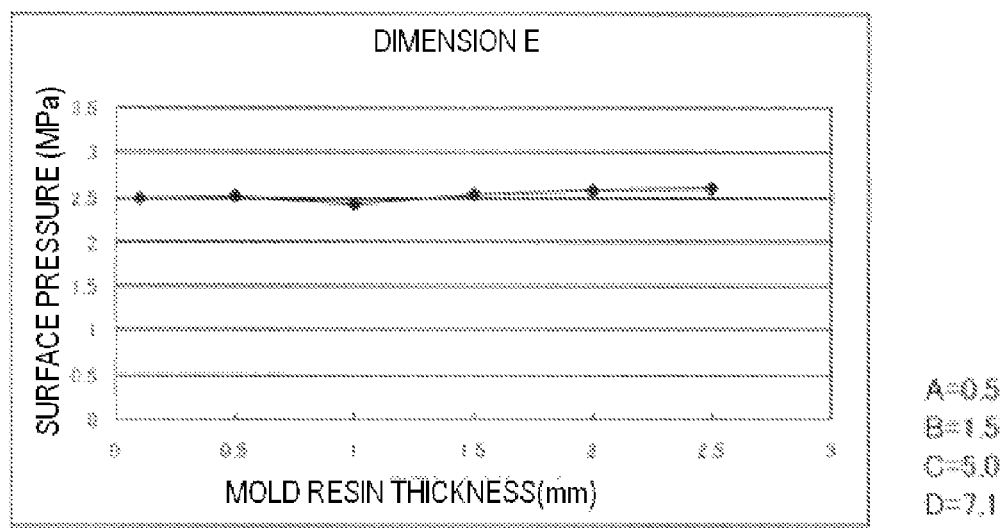

FIG. 5C shows the change of the surface pressure at the measurement point in the case where E is changed in the range from 0.5 to 2.5 mm in the state of A=0.5 mm, B=1.5 mm, C=5.0 mm, and D=7.1 mm.

Effects of the Invention

In the circuit section 10 of the $NO_x$ sensor 2 of the gas sensing apparatus 1 of the embodiment, the enclose portion 15a which encloses the second circumferential side surface 13a of the base portion 13 of the output base 11 is disposed in the seal portion 15. When contraction of the seal portion 15 occurs, therefore, the enclose portion 15a contracts to further compress the circumference of the base portion 13. Consequently, the enclose portion 15a hardly peels off from the second circumferential side surface 13a, and the seal portion 15 can be suppressed from peeling off from the output base 11.

Moreover, the increased compression of the enclose portion 15a against the circumference of the base portion 13 enhances the close contact force between the enclose portion 15a and the second circumferential side surface 13a, and the waterproof effect of the seal portion 15 can be strengthened.

From the results of the simulation of the surface pressure according to the dimensions of the seal portion 15 and the output base 11, the following effects were noted.

Namely, the results of the simulation in the case where the length A was changed (FIG. 4B) show that, when A is equal to or shorter than 0.5 mm, the increasing degree of the surface pressure with the increase of A is high. From this, it is known that the thickness of the enclose portion 15a is preferably set to 0.5 mm or more.

The results of the simulation in the case where the length B was changed (FIG. 4C) show that, as B is made longer, the surface pressure at the measurement point is higher. From this, it is known that the length between the first and second circumferential side surfaces 12b, 13a in the output base 11 is preferably set as long as possible.

The results of the simulation in the case where the length C was changed (FIG. 5A) shows that, when C is equal to or shorter than 2 mm, the increasing degree of the surface pressure with the increase of C is high. From this, it is known that the length from the mount surface 12a of the output base 11 to the peripheral edge of the support surface 13b is preferably set to 2 mm or more. In the case where the width D was changed, the surface pressure at the measurement point was not much changed. Therefore, it is known that the width D is not a parameter which particularly affects the surface pressure. Also in the case where the length E was changed, the surface pressure at the measurement point was not much changed. However, it is known that, when the length of the enclose portion 15a in the projection direction of the pedestal portion 12 is set to 0.1 mm or more, a high surface pressure can be obtained.

Figure 6:
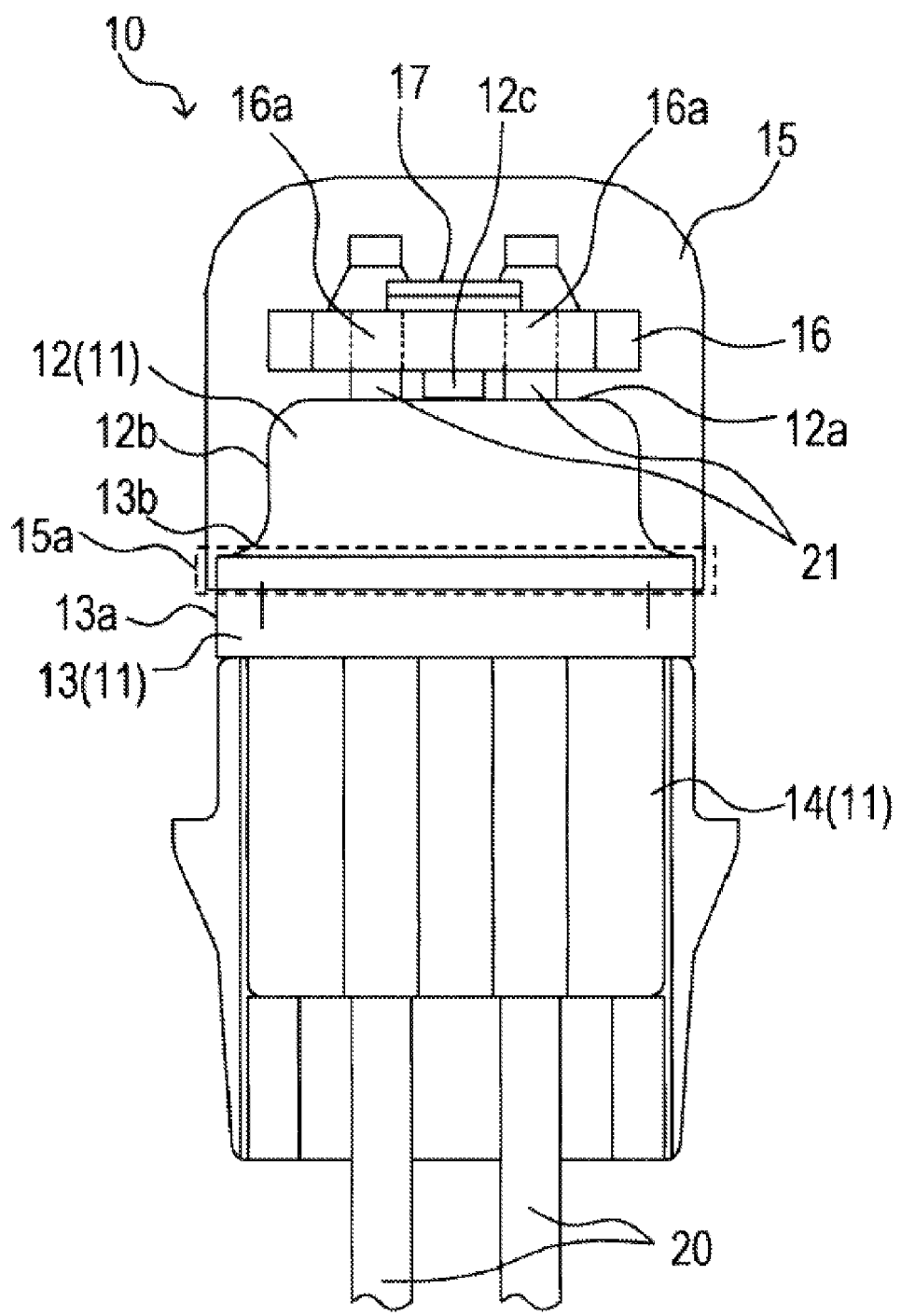
FIG. 6 is a side elevation view of a circuit section of a modification.
Figure 7:
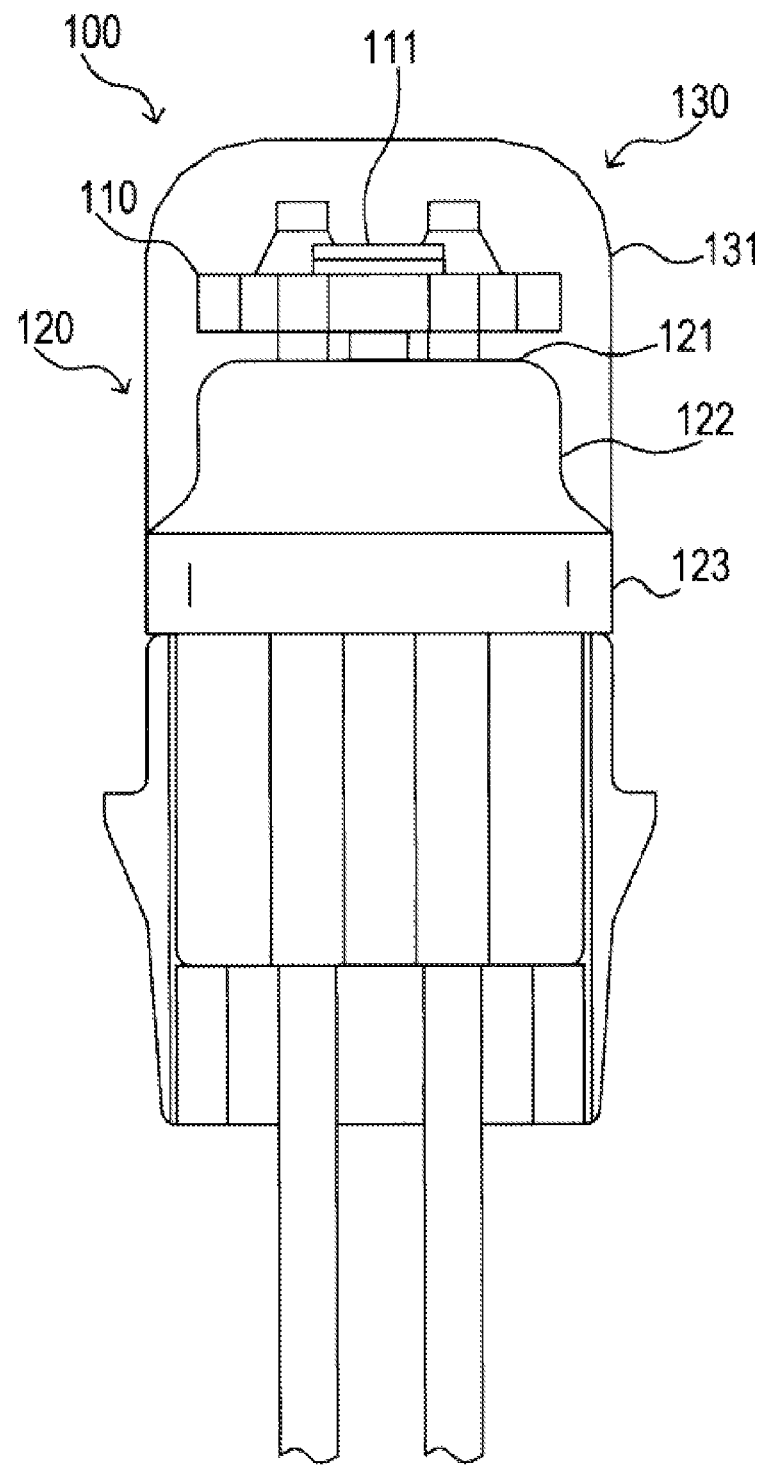
FIG. 7 is a side elevation view of a circuit section of a $NO_x$ sensor disclosed in Patent Reference 1.

Other Embodiments (1) In the gas sensing apparatus 1 of the embodiment, the chamfered portion 13c is formed in the peripheral edge of the support surface 13b of the base portion 13 in the output base 11 of the circuit section 10. The invention is not limited thereto, and the chamfered portion may not be formed. FIG. 6 is a side elevation view of the circuit section 10 in the case where the chamfered portion is not formed in the peripheral edge of the support surface 13b. Also in such a case, it is possible to attain similar effects.

(2) Although the embodiment has been described by exemplifying the gas sensing apparatus 1 which detects the concentration of $NO_x$, the invention is not limited thereto. When correction based on individual information of a sensing element is performed, the configuration of the circuit section 10 in the embodiment can be applied to a gas sensing apparatus which detects the existence or concentration of a specific gas in a detection target gas. A soot sensor which detects the concentration of soot in a detection target gas is known. Also in such a soot sensor, correction based on individual information of a sensing element may be performed. The configuration of the circuit section 10 in the embodiment can also be applied to such a soot sensor.

Correspondence with Claims

The correspondence between the terms used in the description of the embodiment and those used in the appended claims will be described.

The second circumferential side surface 13a of the base portion 13 of the output base 11 corresponds to the side surface of the base portion.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2011-088376 filed Apr. 12, 2011, the disclosure of which is incorporated herein by reference in its entirety.

What is claimed is:

1. A sensor including:
a sensing element which detects a specific component in a detection target gas;
a circuit board on which a storage medium is mounted, the storage medium storing individual information related to the sensing element;
an output base having: a pedestal portion on which the circuit board is placed; and a base portion in which a support surface is formed, the pedestal portion projecting from a middle part of the support surface; and
a seal portion which is arranged above the support surface in a state where the seal portion covers the pedestal portion from upper and lateral sides, and which maintains the circuit board watertight,
wherein the seal portion has an enclose portion which, in a state where the enclose portion protrudes from a peripheral edge of the support surface of the base portion, to a side surface of the base portion intersecting with the support surface at the peripheral edge, encloses the side surface along the peripheral edge.

2. The sensor as claimed in claim 1, wherein
a chamfered portion is formed in the peripheral edge of the support surface of the base portion.

3. The sensor as claimed in claim 1, wherein
the enclose portion has a length of at least 0.1 mm in the projection direction of the pedestal portion.

4. The sensor as claimed in claim 1, wherein
the enclose portion has a thickness of at least 0.1 mm.

* * * * *